(12) United States Patent
Fleming et al.

(10) Patent No.: US 10,929,963 B2
(45) Date of Patent: Feb. 23, 2021

(54) OCT IMAGE PROCESSING

(71) Applicant: Optos PLC, Dunfermline Fife (GB)

(72) Inventors: Alan Duncan Fleming, Dunfermline Fife (GB); Gonzalo Muyo, Dunfermline Fife (GB); Michael Verhoek, Dunfermline Fife (GB)

(73) Assignee: OPTOS PLC, Dunfermline (GB)

( * ) Notice: Subject to any disclaimer, the term of this patent is extended or adjusted under 35 U.S.C. 154(b) by 41 days.

(21) Appl. No.: 16/409,179

(22) Filed: May 10, 2019

(65) Prior Publication Data

US 2019/0347774 A1    Nov. 14, 2019

(30) Foreign Application Priority Data

May 11, 2018    (EP) ..................... 18171806

(51) Int. Cl.
*G06T 7/73*    (2017.01)
*G06T 5/00*    (2006.01)
(Continued)

(52) U.S. Cl.
CPC .............. *G06T 5/006* (2013.01); *A61B 3/102* (2013.01); *A61B 3/12* (2013.01); *A61B 5/0066* (2013.01);
(Continued)

(58) Field of Classification Search
CPC ..... G06T 5/006; G06T 3/0012; G06T 7/0012; G06T 7/73; A61B 3/12; A61B 3/0025
See application file for complete search history.

(56) References Cited

U.S. PATENT DOCUMENTS 9,149,181 B2    10/2015    Matsumoto et al.
9,384,582 B2    7/2016    Izatt et al.
(Continued)

FOREIGN PATENT DOCUMENTS

JP    2012 148003 A    8/2012
JP    2013 154121 A    8/2013
(Continued)

OTHER PUBLICATIONS

Anthony N. Kuo et al.: "Posterior Eye Shape Measurement With Retinal OCT Compared to MRI," Investigavtive Ophthalmology & Visual Science, vol. 57, No. 9, Jul. 2016. DOI:10.1167/iovs.15-18886.
(Continued)

*Primary Examiner* — Sam Bhattacharya
(74) *Attorney, Agent, or Firm* — DeLucia, Mlynar & Alicandro LLP

(57) ABSTRACT

An apparatus for rendering optical coherence tomography, OCT, retinal image data, acquired by an OCT scanner scanning a retina of an eye over a range of scan locations, wherein each scan location is associated with a respective coordinate in a first coordinate system, and each pixel of the rendered OCT retinal image data is associated with a respective coordinate in a second coordinate system different from the first coordinate system. The apparatus comprises a communication module arranged to receive the OCT retinal image data, and a coordinate-determining module arranged to determine values of coordinates in the second coordinate system of pixels in the received OCT retinal image using a transformation from coordinates in the first to second coordinate system. The apparatus further comprises an interpolation module arranged to interpolate between values of pixels at the determined values to calculate values of the pixels of the rendered OCT retinal image data.

20 Claims, 10 Drawing Sheets

(51) Int. Cl.
*A61B 3/10* (2006.01)
*A61B 3/12* (2006.01)
*A61B 5/00* (2006.01)
*G06T 3/00* (2006.01)
*G06T 7/00* (2017.01)

(52) U.S. Cl.
CPC .......... *G06T 3/0012* (2013.01); *G06T 7/0012* (2013.01); *G06T 7/73* (2017.01); *G06T 2207/10101* (2013.01); *G06T 2207/30041* (2013.01)

(56) References Cited

U.S. PATENT DOCUMENTS

| | | | |
|---|---|---|---|
| 9,560,962 | B2 | 2/2017 | Namiki et al. |
| 9,593,933 | B2 | 3/2017 | Oritz Egea et al. |
| 2003/0103212 | A1 | 6/2003 | Westphal et al. |
| 2014/0100442 | A1 | 4/2014 | Begin et al. |

FOREIGN PATENT DOCUMENTS

| | | |
|---|---|---|
| JP | 2015 104582 A | 6/2015 |
| JP | 2017113146 A | 6/2017 |
| JP | 201805117 A | 4/2018 |
| WO | 2014/053824 A1 | 4/2014 |

OTHER PUBLICATIONS

Kuo AN et al.: "Correction of ocular shape in retinal optical coherence tomography and effect on current clinical measures" Am J Ophthalmol. Aug. 2013;156(2):304-11. https://www.ncbi.nlm.nih.gov/pubmed/23659972.

Kyungmoo Lee et al.: "Adjustment of the Retinal Angle in SD-OCT of Glaucomatous Eyes Provides Better Intervisit Reproducibility of Peripapillary RNFL Thickness," Invest Ophthalmol Vis Sci. Jul. 2013; 54(7): 4808-4812. https://www.ncbi.nlm.nih.gov/pmc/articles/PMC3720146/.

Miri MS et al.: "Incorporation of gradient vector flow field in a multimodal graph-theoretic approach for segmenting the internal limiting membrane from glaucomatous optic nerve head-centered SD-OCT volumes," Comput Med Imaging Graph. Jan. 2017;55:87-94. https://www.ncbi.nlm.nih.gov/pubmed/27507325.

Extended European Search Report (EESR) from European Application No. 18171806.5, dated Feb. 18, 2019.

Japanese Office Action Issued in Japanese Application No. 2019-090481, dated Jun. 23, 2020. [English Translation of Japanese Office Action Attached].

OCT IMAGE PROCESSING

This application claims benefit of European Patent Application No. 18 171 806.5, filed May 11, 2018, which is incorporated herein by reference in its entirety. To the extent appropriate, a claim of priority is made to the above-disclosed application.

TECHNICAL FIELD

The present invention generally relates to the field of image processing and, more particularly, to the rendering of optical coherence tomography images of a retina in order to reduce geometric distortion.

BACKGROUND

Optical coherence tomography (OCT) of the retina is able to generate two-dimensional tomographic (within the imaging plane) or three-dimensional images of the retina. Such images are widely used clinically to observe the internal structure of the retina, optic nerve head and other structures of the eye. OCT scanners can be used to make measurements of retinal layer thicknesses and to observe abnormalities such as oedema, retinal detachments, macular holes and tumours.

OCT scanners conventionally generate an image over a region of the eye by scanning a laser beam across a range of deflection angles. There may, for example, be two beam deflection devices that are configured to deflect the beam in nominally horizontal and vertical directions.

The data obtained at an instantaneous position of the laser beam as it penetrates the retina is known as an A-scan. Images from such devices are conventionally generated by aligning A-scan data to produce two- or three-dimensional images. There are conventionally linear relationships between the timing of each A-scan and the pixel coordinates at which the captured data is rendered.

SUMMARY

The conventional image rendering outlined above will not generate a geometrically true (that is, an angle-preserving, isometrically-scaled) image of the actual retina because (1) the angle of incidence of the laser beam on the retina varies during the scanning process, (2) there is non-linearity in the optics of the imaging device, and (3) there is spatial and angular variation in the optical properties of the eye. An image rendered with a linear relationship between rendered location and the time of capture will contain some distortion. When imaging a narrow field of retinal view at the posterior pole of the eye, such distortions may be small enough to be ignored. However, when imaging a wider field of retinal view or one that is displaced away from the posterior pole, the geometric distortion resulting from such a naïve image rendering may be significant.

The inventors of the present invention have devised a means to produce a geometrically accurate rendering of OCT images of the retina regardless of the width of the field-of-view or whether the location of the scan is central or in the periphery of the retina.

More particularly, the inventors have devised a method of rendering OCT retinal image data, which has been acquired by an OCT scanner scanning a retina of an eye over a range of scan locations, wherein each of the scan locations is associated with a respective coordinate in a first coordinate system ("capture coordinate system"), and each pixel of the rendered OCT retinal image data is associated with a respective coordinate in a second coordinate system ("rendering coordinate system") that is different from the first coordinate system. The method comprises receiving the OCT retinal image data acquired by the OCT scanner, determining values of coordinates in the second coordinate system of pixels in the received OCT retinal image using a transformation from coordinates in the first coordinate system to coordinates in the second coordinate system, and interpolating between values of the pixels at the determined values of coordinates in the second coordinate system to calculate values of the pixels of the rendered OCT retinal image data.

The inventors have further devised a method of rendering OCT retinal image data, which has been acquired by an OCT scanner scanning a retina of an eye over a range of scan locations, wherein each of the scan locations is associated with a respective coordinate in a first coordinate system, and each pixel of the rendered OCT retinal image data is associated with a respective coordinate in a second coordinate system that is different from the first coordinate system. The method comprises receiving the OCT retinal image data acquired by the OCT scanner, and processing a pixel array using the received OCT retinal image data to generate the rendered OCT retinal image data by: determining values of coordinates in the second coordinate system of pixels in the received OCT retinal image using a transformation from coordinates in the first coordinate system to coordinates in the second coordinate system; interpolating between the determined values of coordinates in the second coordinate system to calculate values of coordinates of the pixels in the pixel array in the first coordinate system; and using the calculated values of coordinates of the pixels in the pixel array in the first coordinate system to interpolate between values of the pixels of the received OCT retinal image data to calculate values of the pixels in the pixel array.

The inventors have further devised a method of rendering OCT retinal image data, which has been acquired by an OCT scanner scanning a retina of an eye over a range of scan locations, wherein each of the scan locations is associated with a respective coordinate in a first coordinate system, and each pixel of the rendered OCT retinal image data is associated with a respective coordinate in a second coordinate system that is different from the first coordinate system. The method comprises receiving (S10) the OCT retinal image data acquired by the OCT scanner, and processing a pixel array using the received OCT retinal image data to generate the rendered OCT retinal image data by: determining, for each pixel of the pixel array, a respective coordinate in the first coordinate system using a transformation from coordinates in the second coordinate system to coordinates in the first coordinate system; and calculating values of the pixels of the pixel array by using the determined coordinates in the first coordinate system to interpolate between values of pixels of the received OCT retinal image data.

The inventors have further devised a non-transitory computer-readable storage medium or a signal carrying computer program instructions which, when executed by a computer, cause the computer to perform one or more of the methods set out above.

The inventors have further devised an apparatus for rendering OCT retinal image data, which has been acquired by an OCT scanner scanning a retina of an eye over a range of scan locations, wherein each of the scan locations is associated with a respective coordinate in a first coordinate system, and each pixel of the rendered OCT retinal image data is associated with a respective coordinate in a second coordinate system that is different from the first coordinate system. The apparatus comprises a communication module arranged to receive the OCT retinal image data acquired by the OCT scanner, and a coordinate-determining module arranged to determine values of coordinates in the second coordinate system of pixels in the received OCT retinal image using a transformation from coordinates in the first coordinate system to coordinates in the second coordinate system. The apparatus further comprises an interpolation module arranged to interpolate between values of the pixels at the determined values of coordinates in the second coordinate system to calculate values of the pixels of the rendered OCT retinal image data.

The inventors have further devised an apparatus for rendering OCT retinal image data, which has been acquired by an OCT scanner scanning a retina of an eye over a range of scan locations, wherein each of the scan locations is associated with a respective coordinate in a first coordinate system, and each pixel of the rendered OCT retinal image data is associated with a respective coordinate in a second coordinate system that is different from the first coordinate system. The apparatus comprises a communication module arranged to receive the OCT retinal image data acquired by the OCT scanner, and a coordinate-determining module arranged to determine values of coordinates in the second coordinate system of pixels in the received OCT retinal image using a transformation from coordinates in the first coordinate system to coordinates in the second coordinate system. The apparatus further comprises an interpolation module arranged to process a pixel array using the received OCT retinal image data to generate the rendered OCT retinal image data by: interpolating between the determined values of coordinates in the second coordinate system to calculate values of coordinates of the pixels in the pixel array in the first coordinate system; and using the calculated values of coordinates of the pixels in the pixel array in the first coordinate system to interpolate between values of the pixels of the received OCT retinal image data to calculate values of the pixels in the pixel array.

The inventors have further devised an apparatus for rendering OCT retinal image data, which has been acquired by an OCT scanner scanning a retina of an eye over a range of scan locations, wherein each of the scan locations is associated with a respective coordinate in a first coordinate system, and each pixel of the rendered OCT retinal image data is associated with a respective coordinate in a second coordinate system that is different from the first coordinate system. The apparatus comprises a communication module arranged to receive the OCT retinal image data acquired by the OCT scanner, and a coordinate-determining module arranged to determine, for each pixel of a pixel array that is to be processed to generate the rendered OCT retinal image data, a respective coordinate in the first coordinate system using a transformation from coordinates in the second coordinate system to coordinates in the first coordinate system. The apparatus further comprises an interpolation module arranged to calculate values of the pixels of the pixel array by using the determined coordinates in the first coordinate system to interpolate between values of pixels of the pixel array.

BRIEF DESCRIPTION OF THE DRAWINGS

Embodiments of the invention will now be explained in detail, by way of non-limiting example only, with reference to the accompanying figures, in which.

DETAILED DESCRIPTION OF EMBODIMENTS

Embodiments of the present invention will now be described in detail with reference to the accompanying drawings.

The following notation is used in the description of embodiments provided below:

The configuration of the OCT scanner described herein is defined by scan parameters H, V, and D, where H and V are the horizontal and vertical scan positions or control signals, and D is optical path distance. The configuration of the OCT scanner in terms of these parameters is denoted (H, V, D).

The captured image data, which is received by the apparatus for rendering OCT retinal image data described herein, is denoted $I_{cap}$, and pixel coordinates in a pixel coordinate system of the captured image are denoted (x, y, z).

The rendered image data is denoted $I_{ren}$, and the pixel coordinates in a pixel coordinate system of the rendered image are denoted (X, Y, Z).

The real-world coordinate system used in system modelling in some of the embodiments is denoted (A, B, C), and the real-world coordinate system used for the image rendering is denoted (A', B', C'), with Cartesian or spherical coordinate systems being taken as examples.

For each of the above coordinate systems, subscripts "cap" and "ren" are used in the description of embodiments provided below, to denote values of the coordinates in the respective coordinate system of a captured (cap) or rendered (ren) pixel. For example, the coordinate values expressed using coordinate system (A', B', C') of a pixel in the captured image are denoted $(A'_{cap}, B'_{cap}, C'_{cap})$. As another example, the values of pixel coordinates (x, y, z) in the pixel coordinate system of the rendered image are denoted $(x_{ren}, y_{ren}, z_{ren})$.

Embodiment 1

Figure 1:
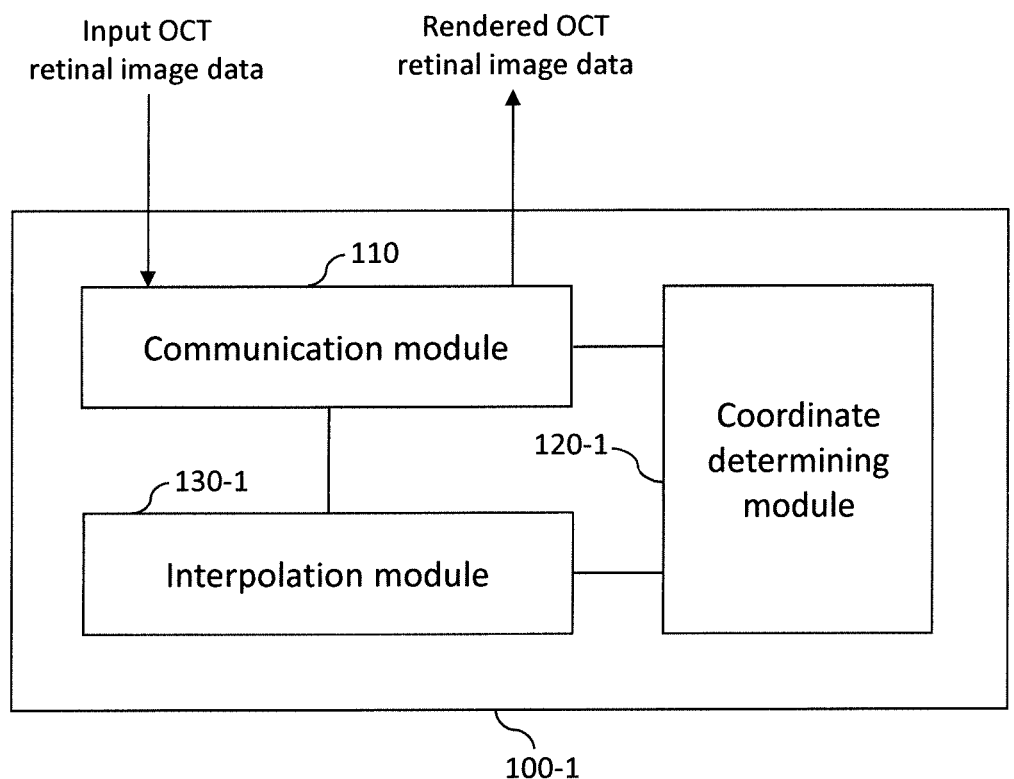
FIG. 1 is a schematic illustration of an apparatus for rendering OCT retinal image data according to a first embodiment of the invention.

FIG. 1 is a schematic illustration of an apparatus 100-1 for rendering OCT retinal image data according to a first embodiment of the invention. The OCT retinal image data processed by the apparatus 100-1 can be acquired by any suitable OCT scanner known to those skilled in the art, which acquires the OCT retinal image data during the course of an OCT scan it performs, where the scan covers a range of scan locations in the patient's eye.

The OCT scanner may, for example, be provided in the form of a combined scanning laser ophthalmoscope (SLO) and OCT imaging system, as described in International Patent Application No. PCT/BG2013/052556 (published as WO2014/053824 A1), the contents of which are incorporated herein by reference in their entirety. The described wide-field SLO-OCT imaging system comprises two scanning elements that can be independently rotated about respective rotation axes to deflect a sample beam of collimated light from a light source, such as a superluminescent diode (SLD) or the like, along different scan axes to perform two-dimensional scans of the surface of the retina and 'slices' of its interior. The scan axes are typically orthogonal and comprise a horizontal axis (H-axis) and a vertical axis (V-axis). For each of a plurality of values of an optical path distance, D, from the light source to the retina, the OCT scanner interferes a reflection of the sample beam from the retina with a reference beam, and measures the intensity of the interfered beams for each of a plurality of two-dimensional scan locations that are covered by the scan.

Each of these scan locations is associated with corresponding OCT scan parameter values that are indicative of the respective scan location. More particularly, where a one-dimensional scan is performed along the H-axis or the V-axis, for example, each scan location along the H-axis (or V-axis, as the case may be) is associated with a value of a scan parameter, H (or V, as the case may be), that is indicative of that scan location, such as a corresponding deflection angle of the scanning element which scans the sample beam along the H-axis (or V-axis, as the case may be), a control signal for causing the scanning element to achieve such deflection angle, or similar operational parameter of the OCT scanner. The deflection angle may be measured or determined from calibration or optical system modelling, for example. By extension, in the case of a two-dimensional scan being performed along both the H and V axes, each scan location is associated with a respective pair of scan parameter values that are indicative of that scan location, such as corresponding deflection angles (again, as measured or as determined from calibration or optical system modelling) of the two scanning elements, control signals for causing the scanning elements to achieve such deflection angles, or the like.

The OCT scanner thus obtains a plurality of OCT measurements in a depth direction of the retina (i.e. along the direction of the beam, at different values of D) for each two-dimensional scan location represented by respective values of H and V, with each such set of OCT measurements (acquired for any given value of H and any given value of V) being widely referred to as an "A-scan", as noted above. By acquiring a plurality of A-scans at points along one of the two-dimensional scan axes (e.g. a direction along the designated H-axis), the OCT scanner can acquire what is widely referred to as a "B-scan", and by acquiring a plurality of B-scans at points along the remaining two-dimensional scan axis (in this example, the designated V-axis), the OCT scanner can acquire what is known as a "C-scan".

The image processing operations described below make use of a known relationship between each measured intensity value (i.e. pixel value) acquired by the OCT scanner and a corresponding set of OCT scan parameter values that are indicative of the location at which the measurement was performed during the scan. Thus, each pixel value in the OCT retinal image data is associated with a respective coordinate in a machine coordinate system of the OCT scanner, which is defined by a value of D in combination with a value of H and/or a value of V, in accordance with which values the OCT scanner would have been operating when the pixel value was measured. Examples of how this relationship can be determined as provided below.

The retinal image processing operations described in the following relate to the processing not only of OCT retinal image data provided in the form of four-dimensional data sets obtained during the acquisition of C-scans (in which each data element comprises a measurement value and an associated point in a three-dimensional space) but also of three-dimensional data sets associated with B-scans (in which each data element comprises a measurement value and an associated point in a two-dimensional space). The three-dimensional data set of the B-scan can be considered to represent a two-dimensional array of pixels defining a two-dimensional image of a slice through the retina, while the four-dimensional data set of the C-scan data can be considered to represent a three-dimensional array of voxels defining a three-dimensional image of the retina. The image processing method described in the following can transform this raw two/three-dimensional image into a geometrically true rendering, from which more accurate measurements can be made.

The apparatus 100-1 comprises a communication module 110 which is operable to receive the OCT retinal image data acquired by the OCT scanner. The OCT retinal image data may, as in the present embodiment, be stored on any suitable storage medium (such as a CD or DVD, or computer hard disk, for example) after having been acquired by the OCT scanner, and subsequently received from a computer or the like (directly or via a network such as a local area network (LAN) or the Internet, for example) when or after the computer reads the OCT retinal image data from the storage medium. The OCT retinal image data may alternatively be received directly form the OCT scanner as it is being acquired during the performance of a retinal scan.

As will be explained further in the following, each of the scan locations is associated with a respective point defined by values of coordinates in a first coordinate system (also referred to here as the "capture coordinate system") which may, as in the present embodiment, be a first real-world coordinate system denoted by (A, B, C), and which is used in modelling the propagation of light in the OCT scanner. Furthermore, each pixel of the rendered OCT retinal image data may, as in the present embodiment, be associated with a respective point defined by values of coordinates in a second coordinate system (also referred to here as the "rendering coordinate system") which is another real-world coordinate system denoted by (A', B', C'). Examples of real-world coordinate systems are Cartesian coordinate systems, whose coordinates are conventionally denoted (x, y, z), and spherical coordinate systems, whose coordinates are conventionally denoted (r, θ, φ).

The apparatus 100-1 further comprises a coordinate-determining module 120-1 which is arranged to determine values of coordinates in the second coordinate system of pixels in the received OCT retinal image using a transformation between coordinates in the first coordinate system and coordinates in the second coordinate system. The coordinate-determining module 120-1 may, as in the present embodiment, be arranged to determine the values of coordinates in the second coordinate system of pixels in the received OCT retinal image using not only said transformation but also a mapping between (i) at least one set of OCT scan parameter values used during the acquisition of the OCT retinal image data, each set of OCT scan parameter values being indicative of a respective location within the scan, and (ii) coordinate(s) in the first coordinate system corresponding to the at least one set of OCT scan parameter values. An example of how the coordinate-determining module 120-1 may determine the values of coordinates in the second coordinate system of pixels in the received OCT retinal image using such transformation and mapping is described below.

The apparatus 100-1 further comprises an interpolation module 130-1 which is arranged to interpolate between values of the pixels at the values of coordinates in the second coordinate system determined by the coordinate-determining module 120-1 (which will typically be irregularly spaced in the second coordinate system) to calculate values of the pixels of the rendered OCT retinal image data (which will typically be regularly spaced in the second coordinate system, being distributed to define a grid of points). In other words, the interpolation module 130-1 is arranged to process a pixel array using the received OCT retinal image data to generate the rendered OCT retinal image data by interpolating between values of the pixels at the coordinates in the second coordinate system determined by the coordinate-determining module 120-1 to calculate values of the pixels of the pixel array, thereby generating the rendered OCT retinal image data. Further details of this interpolation process are also provided below.

Figure 2:
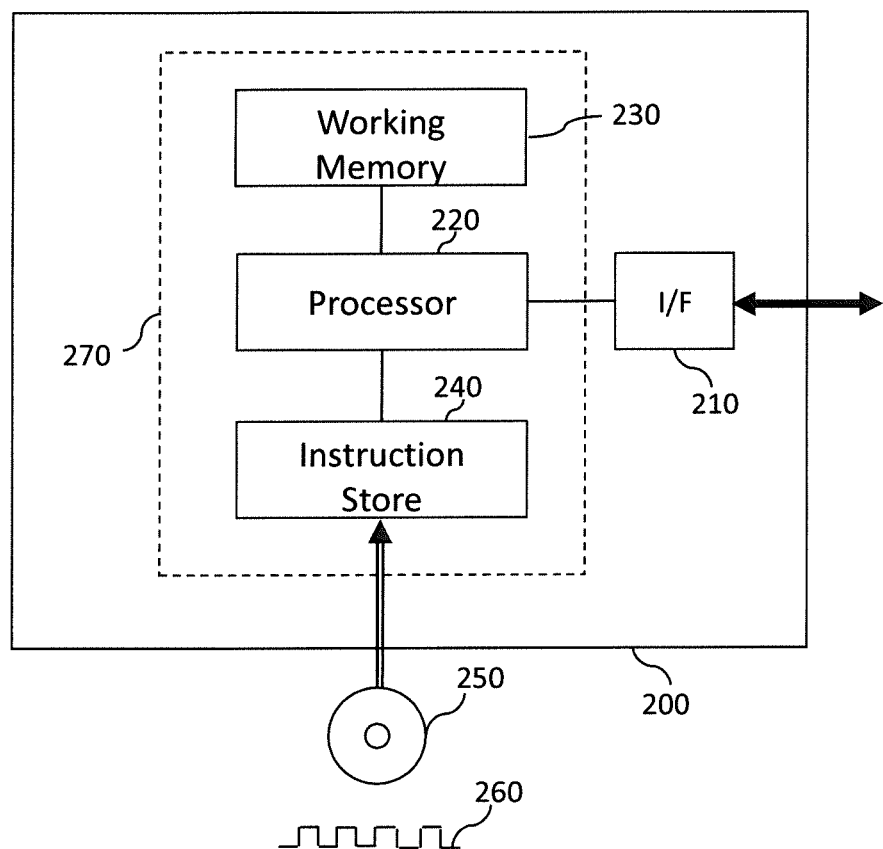
FIG. 2 is a block diagram illustrating an example of hardware configuration of the apparatus for rendering OCT retinal image data according to an embodiment.

FIG. 2 shows an example of how the apparatus 100-1 may be implemented in programmable signal processing hardware. The signal processing apparatus 200 shown in FIG. 2 comprises a communication interface (I/F) 210 for receiving OCT retinal image data acquired by the OCT scanner and outputting rendered OCT retinal image data so that is can be displayed or otherwise processed by the signal processing apparatus or an external device. The signal processing apparatus 200 further comprises a processor (CPU) 220, a working memory 230 (e.g. a random access memory) and an instruction store 240 storing computer-readable instructions which, when executed by the processor 220, cause the processor 220 to perform the processing operations hereinafter described to render the received OCT retinal image data (i.e. process the received OCT data to generate image data representing a two- or three-dimensional image of the portion of the retina that has been scanned to generate the OCT data). The instruction store 240 may comprise a ROM (e.g. in the form of an electrically-erasable programmable read-only memory (EEPROM) or flash memory) which is pre-loaded with the computer-readable instructions. Alternatively, the instruction store 240 may comprise a RAM or similar type of memory, and the computer-readable instructions can be input thereto from a computer program product, such as a computer-readable storage medium 250 such as a CD-ROM, etc. or a computer-readable signal 260 carrying the computer-readable instructions. It should be noted, however, that the apparatus of the embodiments described herein may alternatively be implemented in non-programmable hardware, such as an application-specific integrated circuit (ASIC).

In the present embodiment, the communication I/F 210 is configured to perform the functions of the communication module 110 shown in FIG. 1, while the combination 270 of the hardware components shown in FIG. 2, comprising the processor 220, the working memory 230 and the instruction store 240, is configured to perform the functions of the coordinate-determining module 120-1 and the interpolation module 130-1, which will now be described in detail with reference to FIGS. 3 and 4.

Figure 3:
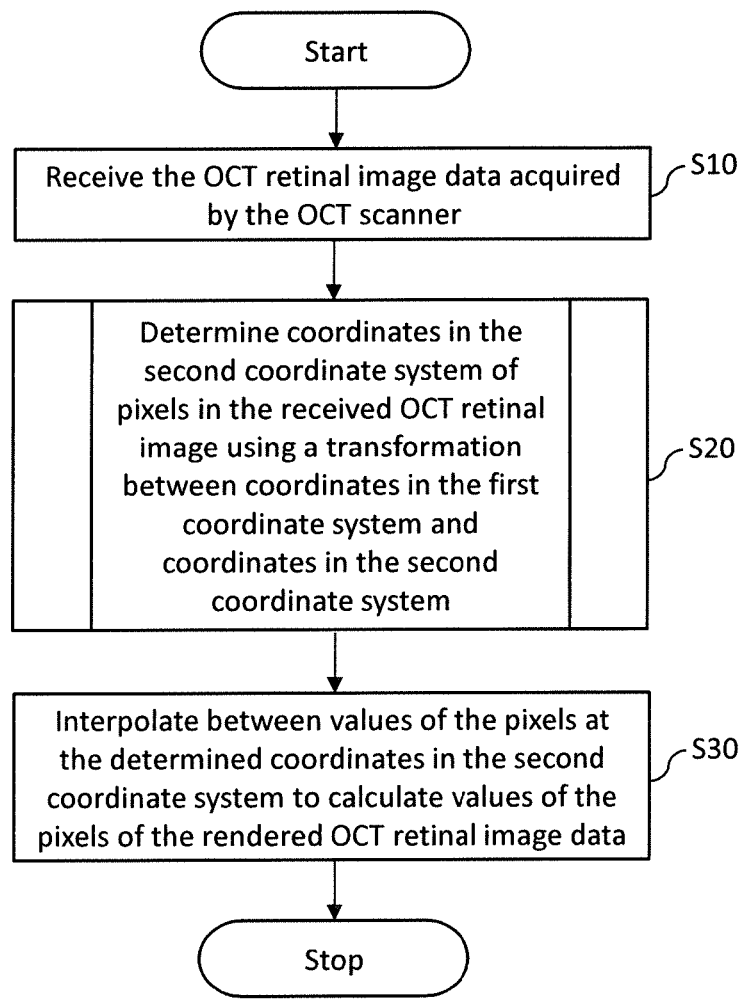
FIG. 3 is a flow diagram illustrating a method of rendering OCT retinal image data according to the first embodiment.

FIG. 3 is a flow diagram illustrating a process by which the apparatus 100-1 renders OCT retinal image data to generate a geometrically true (in other words, an angle-reserving, isometrically-scaled) image of a scanned portion of the retina.

In process S10, the communication module 110 receives the OCT retinal image data acquired by the OCT scanner. In the present embodiment, the received data comprises pixel values indicative of the intensity of an interference signal generated by interfering sample light reflected from the retina with light from a reference arm of the OCT scanner.

By way of example, in the present embodiment, OCT retinal image data representing a two-dimensional (B-scan) OCT image, $I_{cap}$, captured by the OCT scanner is received by the communication module 110. However, as noted above, OCT retinal image data representing a three-dimensional (C-scan) OCT image acquired by the OCT scanner may alternatively be received by the communication module 110. Each column of the received OCT retinal image data corresponds to an A-scan, each having a known and constant value for H and for V. These values for H and V may be received by the communication module 110 together with associated pixel values of the captured image $I_{cap}$, so that the apparatus 100-1 can store the received pixel values in association with the respective received values for H and V. Alternatively, the communication module 110 may receive only the pixel values themselves, with the image rendering algorithm described below determining H and V values for each pixel on the basis of pixel locations of the pixels in an pixel coordinate system (these pixel locations being represented by coordinates x, y and z in the pixel coordinate system) of the received image data, and pre-stored calibration data relating to the OCT scanner which acquired the OCT retinal image data. In this case, the calibration data relates each pixel location in the image data with respective values of H and V. Coordinate $z_c$ represents a coordinate along an image axis which corresponds to the laser beam direction, while x and y represent coordinates along axes that are orthogonal to that image axis.

In process S20, the coordinate-determining module 120-1 determines values of coordinates in the second coordinate system of pixels in the received OCT retinal image using a transformation from coordinates in the first coordinate system to coordinates in the second coordinate system. The coordinate-determining module 120-1 may, as in the present embodiment, also use in this process a mapping between at least one set of OCT scan parameter values used during the acquisition of the OCT retinal image data, and coordinate(s) in the first coordinate system (A, B, C) corresponding to the at least one set of OCT scan parameter values.

This mapping may be derived by using optical system modelling, along with a combined model of the OCT scanner and an assumed eye model, to find the paths of light rays within the OCT scanner to the retina for a range of deflection angles set for the laser beam scanning elements. The assumed eye model may be defined in a variety of ways, such as a specific idealised eye of fixed geometry and dimensions, or a parameterised model whose parameters are derived for a particular eye from ophthalmic biometric data. The end point of the optical system modelling is a mapping between values of the OCT scan parameters H, V, and D and corresponding values of coordinates in the first (real-world) coordinate system (A, B, C). The optical system modelling may be based on knowledge of the optical structure of the OCT scanner and/or on knowledge of the structure of an artificial target and the resulting image when this is imaged by the OCT scanner.

Optical system modelling may be used to determine, for possible values of parameters H and V (that is, for possible light rays), the following data:

1. The values of real-world coordinates where the light ray hits the retina.
2. The direction, as a vector in real-world coordinates, of the light ray within the vitreous of the eye.
3. The distance, known as the optical path distance (D), from the light emitter to the point of intersection of the light ray with the retina.

It should be noted, however, that not all of the above data needs to be obtained in the optical system modelling, and that the results of the optical system modelling can be represented in many different forms.

Regarding the mapping between the values of OCT scan parameter D and corresponding coordinates z in the pixel coordinate system, this can be determined as follows.

The value of D is constant for all pixels with a given value of z, and the spacing between pixels in the $z_{cap}$-direction is known in real distance units. Therefore D=(z−z1)*p, where p is a known value equal to the inter-pixel spacing in the z direction, and z1 is an offset which needs to be determined. The values of z1 can be determined in one of a number of different ways.

For example, pixel values in the received OCT retinal image data may be analysed (e.g. by computer image analysis) to detect a layer of the retina, and the value of z for a subset of image columns at this layer of the retina can be found. At points along this detected layer, the value of D is assumed to be known from the output of optical system modelling. This allows an estimate for z1 to be determined.

As an alternative, z1 may be determined by using information from the control system of the OCT scanner. The optical path length in the reference arm is controlled precisely by the device and hence there is a known relationship between the positional control parameter and z1. This relationship can be determined from knowledge of the design of the OCT scanner or obtained from calibration.

It should be noted, however, that z1 need not be determined explicitly by either of the above (or other) methods; it is the determination of the value of the D for each value of $z_{cap}$, and hence a mapping between the values of OCT scan parameters H, V and D and corresponding coordinates (x, y, z), that is preferably obtained.

Figure 4:
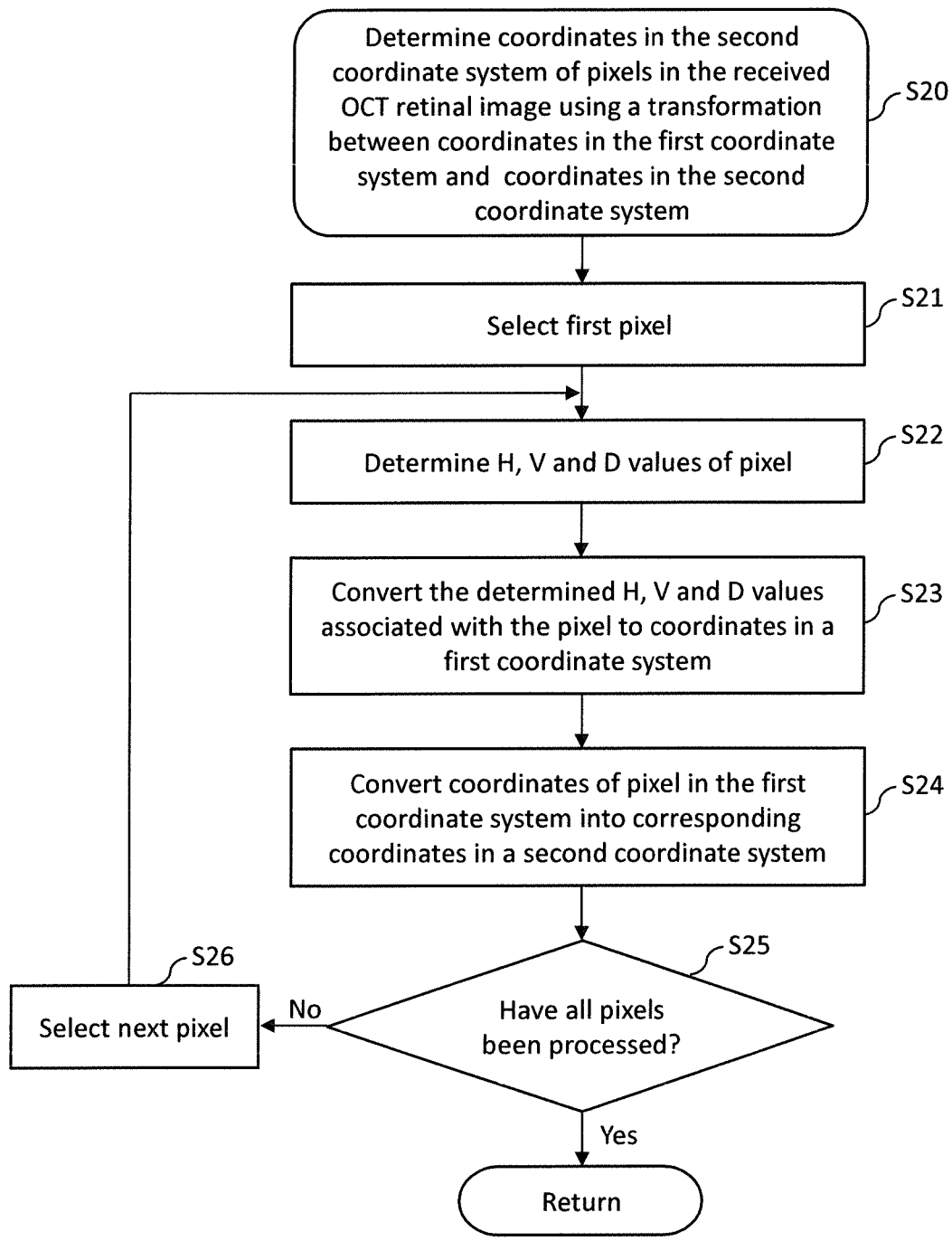
FIG. 4 is a flow diagram showing details of process S20 in FIG. 3.

In order to re-project the coordinates of the OCT retinal image data pixels from the first coordinate system into the second coordinate system, the coordinate-determining module 120-1 uses the determined first mapping between the values of OCT scan parameters H, V and D and corresponding coordinates (x, y, z), and the determined second mapping between values of the OCT scan parameters H, V and D and corresponding coordinates in the first real-world coordinate system (A, B, C), as will now be described with reference to FIG. 4.

FIG. 4 is a flow diagram illustrating an example of how the coordinate-determining module 120-1 can determine the values of coordinates, in the second coordinate system, of pixels of the received OCT retinal image data.

In process S21, a first pixel of the received OCT retinal image data is selected. Then, in process S22, the coordinate-determining module 120-1 determines, for the first pixel being considered in the current iteration, corresponding values of OCT scan parameters H, V and D using the first mapping described above. In process S23, these scan parameter values are converted into corresponding values of coordinates in the first real-world coordinate system (A, B, C) using the (second) mapping between values of the OCT scan parameters and corresponding coordinates in the first real-world coordinate system (A, B, C) described above. Thus, values of the real-world coordinates of pixels in the received OCT retinal image data are determined at this stage of the image rendering process.

Depending on the data available in the output of optical system modelling, the calculation of the pixels' real-world coordinates may be simplified. For example, in a variant of the embodiment where the direction of the light ray within the vitreous of the eye is known as a vector in the real-world coordinate system, the above iteration can be performed for only one pixel in each image column (A-scan). Then, the values of coordinates of pixels in the first real-world coordinate system, ($A_{cap}$, $B_{cap}$, $C_{cap}$), could be calculated for the remaining pixels in the column by iterating over the pixels in the column and adding the direction vector of the light ray scaled by the inter-pixel distance (which is known).

A second real-world coordinate system (A', B', C') is chosen in which to render the OCT retinal image data. This choice may be informed or accomplished in a variety of ways. For example, a Cartesian or spherical coordinate system may be chosen that is standardized across multiple image capture events, or the same as that used in another capture event. This may be appropriate, for example, (a) to facilitate comparison by the user of the current image with another image, or (b) to facilitate comparison by an automated system for disease change detection or image registration using the current image and another image. Alternatively, a Cartesian or spherical coordinate system may be used that is aligned in some optimal way with the captured data. One or more of the axes of the second coordinate system (A', B', C') may be closely aligned with one of more of the axes of the captured data. For example, if a Cartesian coordinate system is used, one axis may align, in some optimal way, with scan direction H and another may align, in some optimal way, with the scan direction V. Alternatively, if a spherical coordinate system is used, then the radial axis may align with the light propagation direction along which D is measured.

Whatever method is used to decide the second real-world coordinate system (A', B', C'), there must be a known relationship between the first and second real-world coordinate systems (A, B, C) and (A', B', C'), so that there is a transformation (A, B, C)⇔(A', B', C') for converting coordinates values from one to the other. For example, this step may require calculation of a homogenized matrix, P, so that the conversion can be performed by matrix multiplication:

$$(A',B',C',1)^T = P(A,B,C,1)^T$$

For image rendering, ranges for pixel coordinate values ($X_{ren}$, $Y_{ren}$, $Z_{ren}$) of pixels in the pixel array that is to be processed to yield the rendered image, and a linear mapping between the second real-world coordinate system (A', B', C') and the rendered pixel grid coordinates (X, Y, Z) are chosen. Each set of pixel coordinates may simply be a set of (integer) values of indices that identify the location of the pixel in the pixel array/grid, or a set of values derived therefrom by any appropriate one-to-one mapping. One way to choose the ranges is to take, in each axis of the catured image data, the minimum and maximum values of its coordinates min ($A'_{cap}$), max($A'_{cap}$), min($B'_{cap}$), max($B'_{cap}$), min($C'_{cap}$), max ($C'_{cap}$), in the second real-world coordinate system (A', B', C'). If the above linear mapping is chosen such that the averages of spacings between $X_{cap}$, $Y_{cap}$, and $Z_{cap}$ corresponding to adjacent captured pixels are approximately unity in each dimension, then the captured information will be well rendered in the rendered image.

In process S24, the determined coordinate values ($A_{cap}$, $B_{cap}$, $C_{cap}$) of the pixel in the first real-world coordinate system (A, B, C) are converted into corresponding coordinate values ($A'_{cap}$, $B'_{cap}$, $C'_{cap}$) in the second real-world coordinate system (A', B', C') using the transformation (A, B, C)⇌(A', B', C') mentioned above.

In process S25, the coordinate-determining module 120-1 determines whether all (or a designated subset of interest) of the pixels in the received retinal image data have been processed. If not, the next pixel is selected in process S26, and the processing loops back to process S22. On the other hand, when it is determined in process S25 that there are no more pixels to process, the processing of S20 is complete, and processing proceeds to S30 in FIG. 3. In this way, the pixels of the received OCT retinal image data are iteratively processed to determine their respective coordinates in the first real-world coordinate system and then re-project these coordinates into the second real-world coordinate system. The values of coordinates ($A'_{cap}$, $B'_{cap}$, $C'_{cap}$) in the second real-world coordinate system (A', B', C') determined in this way will, in general, be irregularly-spaced in this coordinate system.

Referring again to FIG. 3, in process S30, the interpolation module 130-1 interpolates between values of the pixels at the determined values of coordinates ($A'_{cap}$, $B'_{cap}$, $C'_{cap}$) in the second coordinate system (A', B', C') to calculate values of pixels (at coordinate values ($A'_{ren}$, $B'_{ren}$, $C'_{ren}$)) that are to form the rendered OCT retinal image data.

Thus, for the pixels of the pixels array that is to be processed to generate the rendered OCT image data (which, for convenience, are referred to herein simply as pixels of the rendered OCT retinal image data), intensity values $I_{ren}$ of pixels of the rendered OCT retinal image data at regularly-spaced coordinates ($A'_{ren}$, $B'_{ren}$, $C'_{ren}$) in the second real-world coordinate system are determined by interpolating between the known values at the non-regularly-spaced coordinates ($A'_{cap}$, $B'_{cap}$, $C'_{cap}$) of pixels of the received OCT retinal image data $I_{cap}$ that have been projected into the second real-world coordinate system. To do this, the interpolation module 130-1 performs a scatter interpolation; unlike regular interpolation, where values are known at regularly-spaced locations and finding values at locations in-between is straightforward, for scatter interpolation, values are only known at irregularly-spaced locations, and it is more challenging to find values at regularly-spaced locations from these. Nevertheless, methods of performing interpolation on such data are well-known, and include triangulated networks such as based on Delauney triangulation and thin-plate splines.

In the variant of the embodiment mentioned above, the coordinates in the second real-world coordinate system of pixels in the received OCT retinal image data of the A-scan can be determined in process S20 by using the transformation (A, B, C)⇌(A', B', C') and the first mapping to determine the coordinates in the second real-world coordinate system of a first pixel in the received OCT retinal image data of the A-scan, the first pixel being associated with a first set of OCT scan parameter values, and using the transformation (A, B, C)⇌(A', B', C') and a vector in the first real-world coordinate system that is indicative of a direction of a light beam incident on or propagating in the retina of the eye when the OCT scanner operates in accordance with the first set of OCT scan parameter values to determine coordinates in the second real-world coordinate system of remaining pixels in the received OCT retinal image data of the A-scan.

The rendered OCT retinal image data is then output by the communication module 110 so that it can be displayed on any suitable display device (such as a computer screen or the like) and/or processed automatically or under user guidance to determine a dimensional measurement of one or more features of interest in the rendered OCT retinal image data.

An apparatus 100-2 for rendering OCT retinal image data according to a variant of the first embodiment will now be described with reference to FIGS. 5 and 6.

Figure 5:
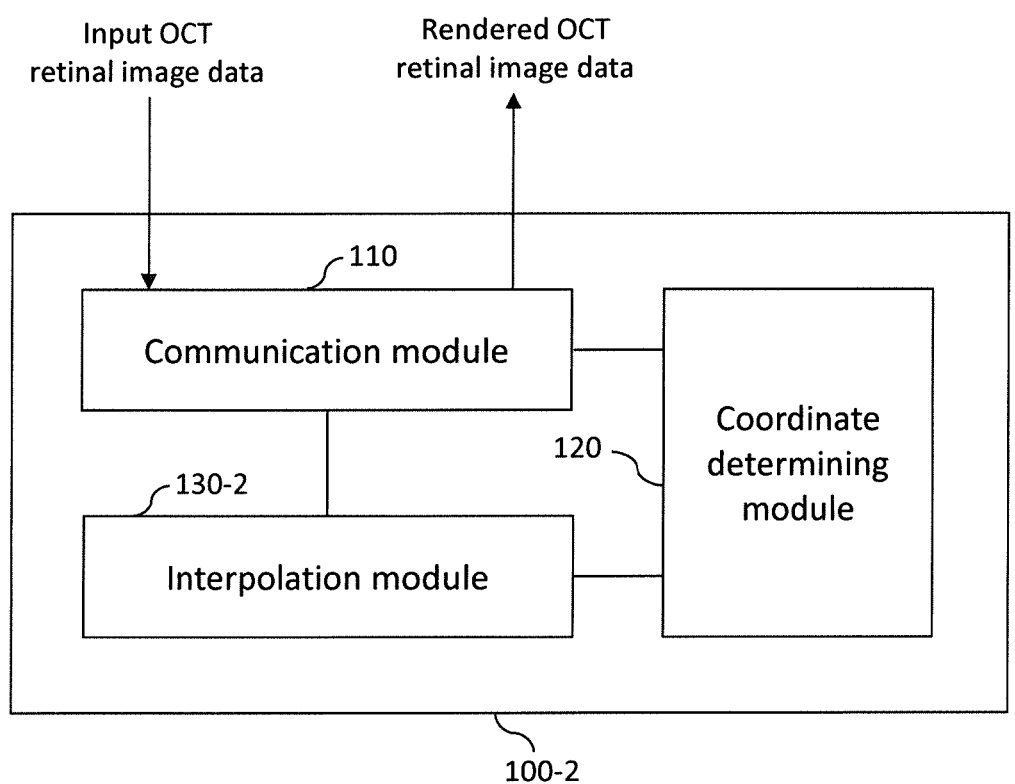
FIG. 5 is a schematic illustration of an apparatus for rendering OCT retinal image data according to a variant of the first embodiment.

The apparatus 100-2 of the variant shown schematically in FIG. 5 differs from the apparatus 100-1 of the first embodiment only by the functionality of the interpolation module 130-2. The implementation of the apparatus 100-2 in signal processing hardware and the functionality its remaining components are the same as in the first embodiment, and will therefore not be described again. The difference in functionality of the interpolation module 130-3 will now be described with reference to FIG. 6.

Figure 6:
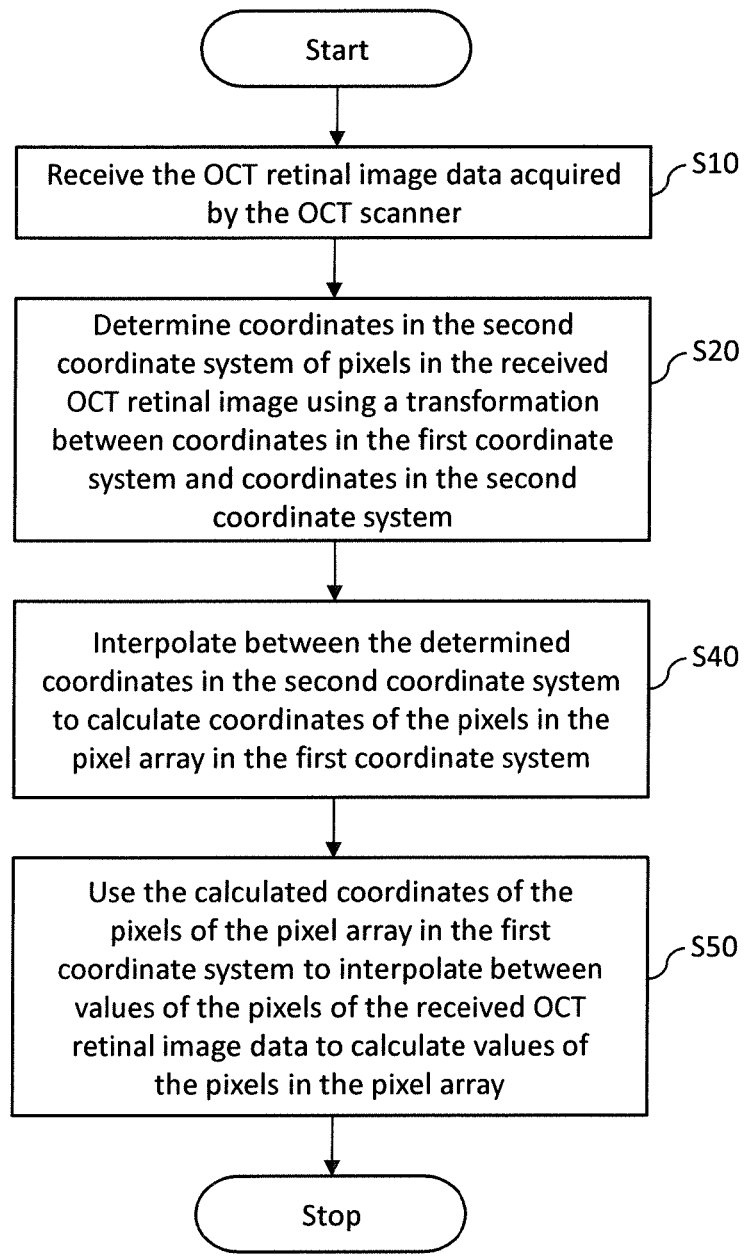
FIG. 6 is a flow diagram illustrating a method of rendering OCT retinal image data according to the variant.

FIG. 6 is a flow diagram illustrating a process by which the apparatus 100-2 renders OCT retinal image data to generate a geometrically true image of a scanned portion of the retina. Processes S10 and S20 are the same as those of the first embodiment. However, the process by which the interpolation module 130-2 of the variant processes a pixel array using the received OCT retinal image data to generate the rendered OCT retinal image data is different to the processing performed by interpolation module 130-1 of the first embodiment, as will now be explained.

In process S40, the interpolation module 130-2 interpolates between the coordinates, in the second real-world coordinate system (A', B', C'), of the pixels of the received OCT retinal image data, to calculate coordinates of the pixels of the pixel array in the first real-world coordinate system (A, B, C). The coordinates of the pixels of the received OCT retinal image data in the second real-world coordinate system (A', B', C') will generally be irregularly-spaced. The interpolation module 130-2 of the variant performs a scatter interpolation on this data using, for example, triangulated networks such as based on Delauney triangulation or thin-plate splines, to determine the coordinates of the pixels of the pixel array in the first real-world coordinate system (A, B, C).

In process S50, the interpolation module 130-2 uses the calculated coordinates of the pixels of the pixel array in the first real-world coordinate system (A, B, C) to interpolate between values of the pixels of the received OCT retinal image data to calculate values of the pixels of the pixel array, thereby generating the rendered OCT retinal image data.

Embodiment 2

An apparatus 100-3 for rendering OCT retinal image data according to a second embodiment of the invention will now be described with reference to FIGS. 7 and 8.

Figure 7:
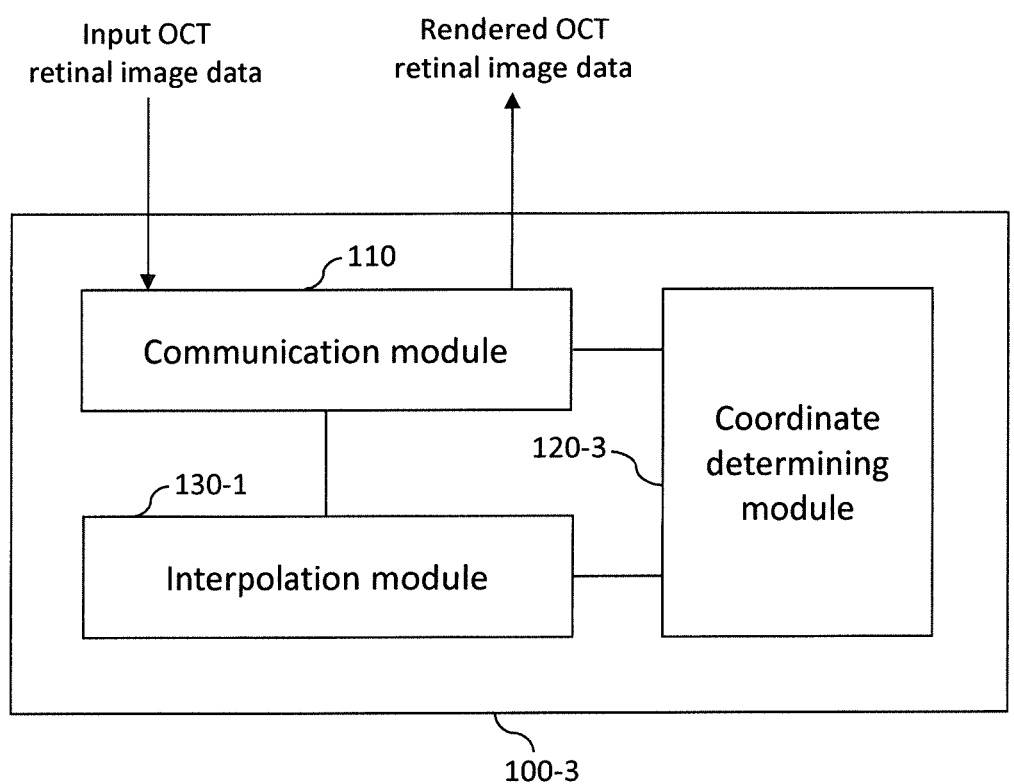
FIG. 7 is a schematic illustration of an apparatus for rendering OCT retinal image data according to a second embodiment of the invention.
Figure 8:
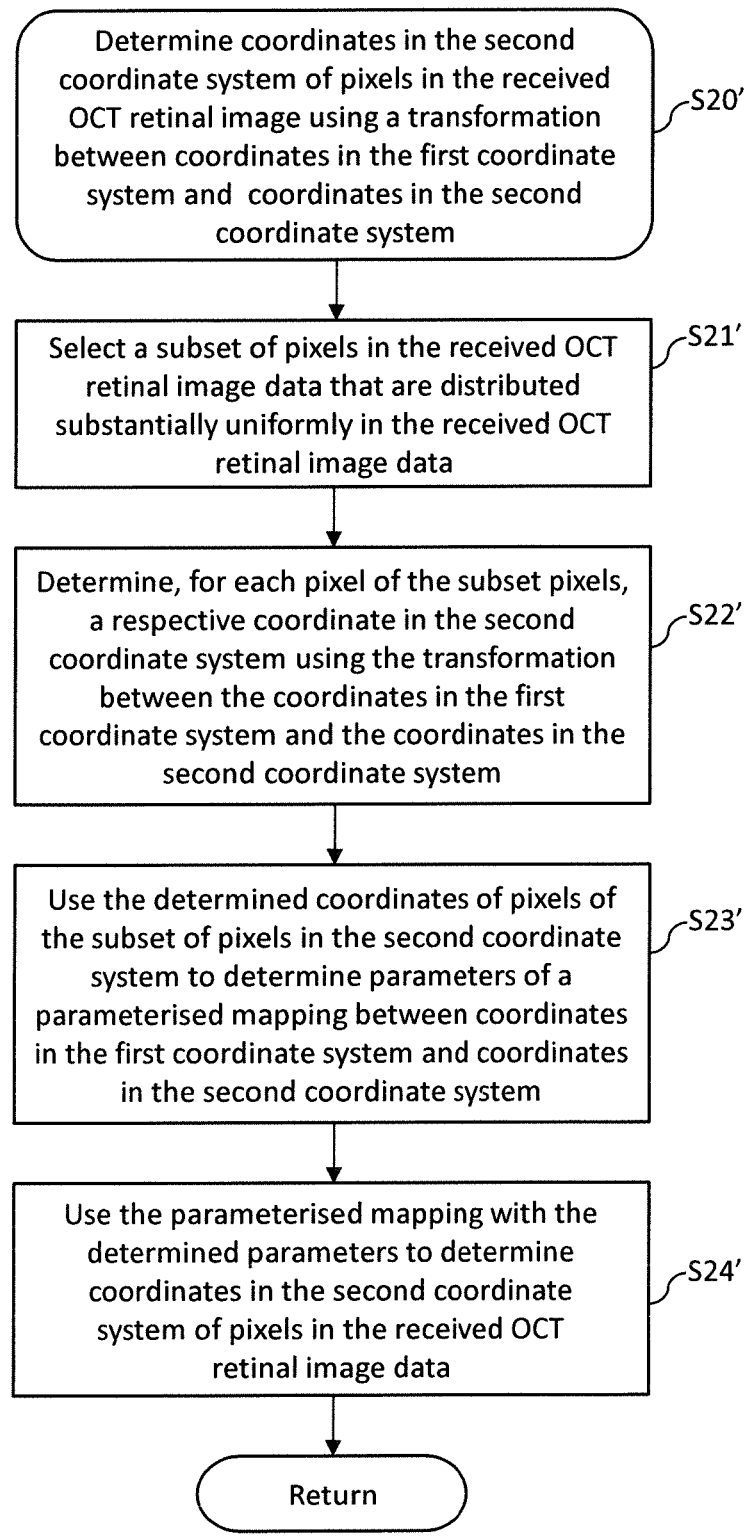
FIG. 8 is a flow diagram illustrating a method of rendering OCT retinal image data according to the second embodiment.

The apparatus 100-3 of the present embodiment shown schematically in FIG. 7 differs from the apparatus 100-1 of the first embodiment only by the functionality of the coordinate-determining module 120-3. The implementation of the apparatus 100-3 in signal processing hardware, the functionality its remaining components, and the possible variations that can be made to the apparatus, are the same as in the first embodiment, and will therefore not be described again.

The process by which the coordinate-determining module 120-3 of the present embodiment determines coordinates in the second coordinate system of pixels in the received OCT retinal image data, in a process S20' that is an alternative to process S20 shown in FIG. 3, will now described with reference to FIG. 8.

In process S21', the coordinate-determining module 120-3 selects a subset of pixels in the received OCT retinal image data that are distributed substantially uniformly (among the pixel locations) in the received OCT retinal image data.

In process S22', the coordinate-determining module 120-3 determines, for each pixel of the subset of pixels, a respective coordinate in the second coordinate system using the transformation between coordinates (x, y, z) in the (first) coordinate system of the received OCT retinal image data and coordinates (X, Y, Z) in the (second) coordinate system of the pixel array that is to be processed to give the rendered image. An 'ideal' mapping is thus obtained using the subset of pixels.

The coordinate-determining module 120-3 may, as in the present embodiment, determine the respective coordinate in the second coordinate system for each pixel of the subset of pixels using: a first mapping for converting the coordinate (x, y, z) of a pixel of the received OCT image data from the first coordinate system to the first real-world coordinate system (A, B, C); a second mapping for converting the coordinate of a pixel in the first real-world coordinate system (A, B, C) to a coordinate in the second real-world coordinate system (A', B', C'); and a third mapping for converting the coordinate (X, Y, Z) of a pixel in the pixel array to a corresponding coordinate in the second real-world coordinate system (A', B', C').

In process S23', the coordinate-determining module 120-3 uses the determined coordinates of pixels of the subset of pixels in the second coordinate system to determine parameters of a parameterised mapping between coordinates (x, y, z) in the first coordinate system and coordinates (X, Y, Z) in the second coordinate system. The parameters for this mapping may be generated by exact fitting, for example by fitting a spline (a piece-wise polynomial). In this case, the subset of points after applying the ideal mapping are substantially the same as those after applying the parameterised mapping. Alternatively, a regression technique may be used to minimise a loss function based on the differences between the subset of points after applying the ideal mapping and those after applying the parameterised mapping.

Finally, in process S24', the coordinate-determining module 120-3 uses the parameterised mapping with the determined parameters to determine coordinates (X, Y, Z) in the second coordinate system of pixels in the received OCT retinal image data.

Embodiment 3

An apparatus 100-4 for rendering OCT retinal image data according to a third embodiment of the invention will now be described with reference to FIGS. 9 and 10.

Figure 9:
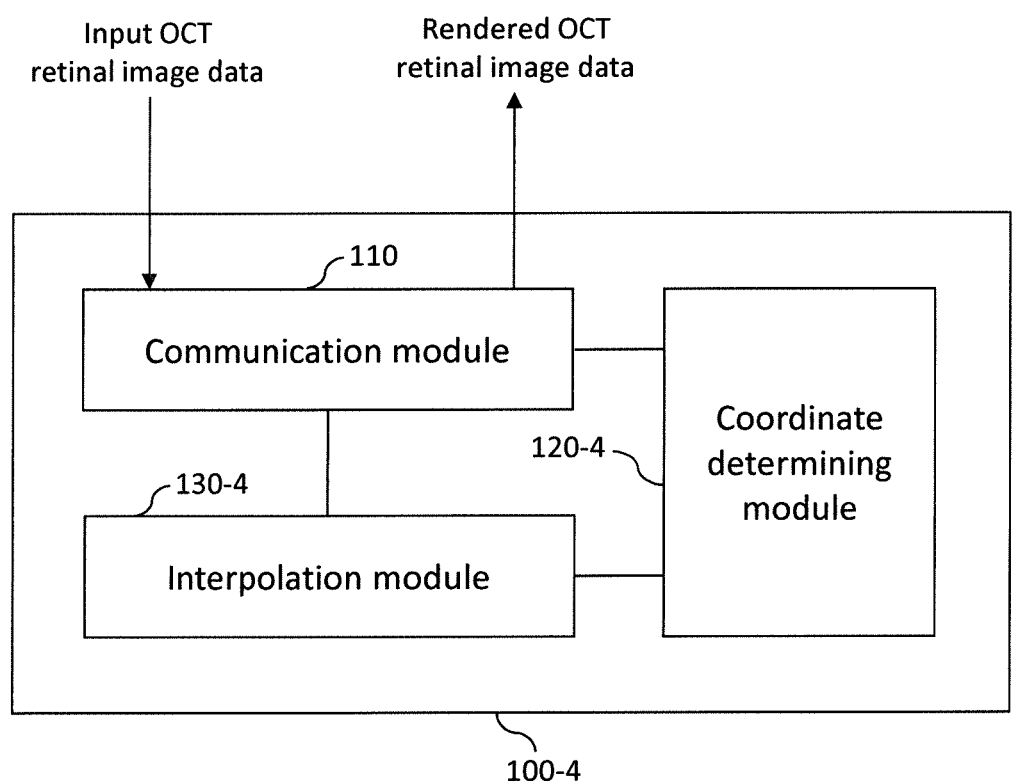
FIG. 9 is a schematic illustration of an apparatus for rendering OCT retinal image data according to a third embodiment of the invention.

The apparatus 100-4 of the present embodiment shown schematically in FIG. 9 differs from the apparatus 100-1 of the first embodiment only by the functionalities of the coordinate-determining module 120-4 and the interpolation module 130-4. The implementation of the apparatus 100-4 in signal processing hardware and the functionality of the communication module 110 are the same as in the first embodiment, and will therefore not be described again.

Figure 10:
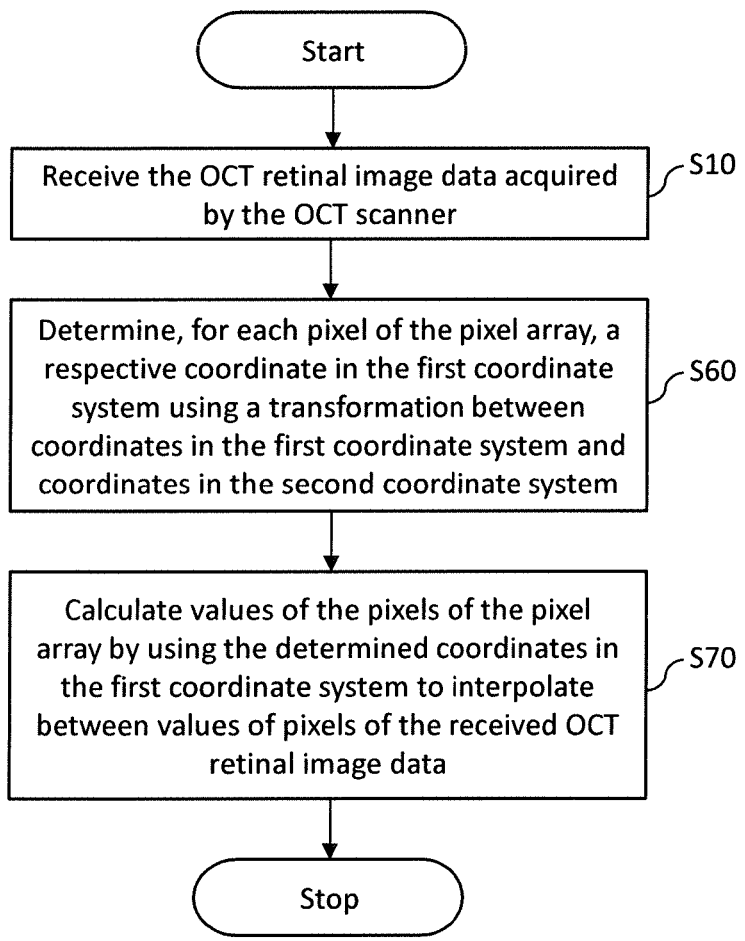
FIG. 10 is a flow diagram illustrating a method of rendering OCT retinal image data according to the third embodiment.

FIG. 10 is a flow diagram illustrating a process by which the apparatus 100-4 renders OCT retinal image data to generate a geometrically true image of a scanned portion of the retina. Process S10 is the same as in the first embodiment. However, the operations performed by the coordinate-determining module 120-4 and the interpolation module 130-4 are different to those performed by the coordinate-determining module 120-1 and the interpolation module 130-1 of the first embodiment, and these will now be described.

In process S60, the coordinate-determining module 120-4 determines, for each pixel of a rendering pixel array that is to be processed to generate the rendered OCT retinal image data, a respective coordinate (x, y, z) in a first coordinate system being that of the received OCT retinal image data, using a transformation from coordinates in a second coordinate system being that of the rendered OCT retinal image data to coordinates in the first coordinate system. Thus, the coordinate ($X_{ren}$, $Y_{ren}$, $Z_{ren}$) in the second coordinate system is converted to a corresponding coordinate ($X_{ren}$, $Y_{ren}$, $Z_{ren}$) in the first coordinate system. The first and second coordinate systems in this embodiment may be defined in any suitable way. For example, each pixel of the received OCT retinal image data may have pixel coordinates in the first coordinate system that are integer values representing the location of the pixel in the two- or three-dimensional array or grid of pixels constituting the received OCT retinal image data, with each set of integer values being associated with respective values of OCT scan parameters H, V and D in the case of a three-dimensional array (or H and D (alternatively V and D) in the case of a two-dimensional array, for example).

The coordinate-determining module 120-4 may, as in the present embodiment, determine the respective coordinate in the first coordinate system for each pixel of the pixel array data using: (i) a first mapping for converting the coordinate values ($X_{ren}$, $Y_{ren}$, $Z_{ren}$) of the pixel of the pixel array in the second coordinate system to coordinate values ($A'_{ren}$, $B'_{ren}$, $C'_{ren}$) in the real-world coordinate system (A', B', C') discussed above; (ii) a second mapping for converting the coordinate values ($A'_{ren}$, $B'_{ren}$, $C'_{ren}$) of the pixel of the pixel array in the real-world coordinate system (A', B', C') to coordinate values ($A_{ren}$, $B_{ren}$, $C_{ren}$) in the other real-world coordinate system (A, B, C) discussed above; (iii) a third mapping for converting the coordinate values ($A_{ren}$, $B_{ren}$, $C_{ren}$) of the pixel of the pixel array in the real-world coordinate system (A, B, C) to a corresponding set of values of OCT scan parameter values ($H_{ren}$, $V_{ren}$, $D_{ren}$) that are indicative of an location within the scan performed by the OCT scanner; and (iv) a fourth mapping for converting the set of OCT scan parameter values to the corresponding coordinate values ($x_{ren}$, $y_{ren}$, $z_{ren}$) of the pixel of the pixel array in the first coordinate system. The range of real-world coordinates to be covered by the rendered image may, as in the present embodiment, be chosen so that a region of interest in (or perhaps all of) the captured data appears in the rendered image. Assuming that the captured data or its region of interest is conceptually a cuboid of data points, one method to obtain the range of coordinates in (A', B', C') to be covered by the rendered image is to estimate ($A'_{ren}$, $B'_{ren}$, $C'_{ren}$) for the data points at the eight corners of this conceptual cuboid of captured data. The extrema of these values of ($A'_{ren}$, $B'_{ren}$, $C'_{ren}$) are suitable values for the extrema of the ranges of (A', B', C') to be covered by the rendered image.

In process S70, the interpolation module 130-4 calculates values of the pixels of the pixel array by using the coordinates in the first real-world coordinate system (A, B, C) or the corresponding coordinate ($x_{ren}$, $y_{ren}$, $z_{ren}$) of the pixel of the pixel array in the first coordinate system determined by the coordinate-determining module 120-4 in process S60 to interpolate between values of pixels of the received OCT retinal image data, thereby generating the rendered OCT retinal image data.

The interpolations performed in this embodiment are based on regular grids for the source data. Therefore, this embodiment may provide a more efficient implementation than the other embodiments described above, since these each include an interpolation whose source data is on an irregular grid.

Although description has been given above of exemplary embodiments of the present invention with reference to the drawings, the specific configuration of the exemplary embodiments are not limited thereto, and encompass designs and the like within a range not departing from the spirit and scope of the present invention.

All publications, patent applications and technical standards mentioned in the present specification are incorporated by reference in the present specification to the same extent as if each individual publication, patent application, or technical standard was specifically and individually indicated to be incorporated by reference.

The invention claimed is:

1. A method of rendering optical coherence tomography, OCT, retinal image data, which has been acquired by an OCT scanner scanning a retina of an eye over a range of scan locations, wherein each of the scan locations is associated with a respective coordinate in a first coordinate system, and each pixel of the rendered OCT retinal image data is associated with a respective coordinate in a second coordinate system that is different from the first coordinate system, the method comprising:
   receiving the OCT retinal image data acquired by the OCT scanner;
   determining values of coordinates in the second coordinate system of pixels in the received OCT retinal image using a transformation from coordinates in the first coordinate system to coordinates in the second coordinate system; and
   interpolating between values of the pixels at the determined values of coordinates in the second coordinate system to calculate values of the pixels of the rendered OCT retinal image data.

2. A method of rendering optical coherence tomography, OCT, retinal image data, which has been acquired by an OCT scanner scanning a retina of an eye over a range of scan locations, wherein each of the scan locations is associated with a respective coordinate in a first coordinate system, and each pixel of the rendered OCT retinal image data is associated with a respective coordinate in a second coordinate system that is different from the first coordinate system, the method comprising:
   receiving the OCT retinal image data acquired by the OCT scanner; and
   processing a pixel array using the received OCT retinal image data to generate the rendered OCT retinal image data by:
      determining values of coordinates in the second coordinate system of pixels in the received OCT retinal image using a transformation from coordinates in the first coordinate system to coordinates in the second coordinate system;
      interpolating between the determined values of coordinates in the second coordinate system to calculate values of coordinates of the pixels in the pixel array in the first coordinate system; and
      using the calculated values of coordinates of the pixels in the pixel array in the first coordinate system to interpolate between values of the pixels of the received OCT retinal image data to calculate values of the pixels in the pixel array.

3. The method according to claim 1, wherein the values of coordinates in the second coordinate system of pixels in the received OCT retinal image are determined using said transformation and a mapping between (i) at least one set of OCT scan parameter values used during the acquisition of the OCT retinal image data, each set of OCT scan parameter values being indicative of a respective location within the scan, and (ii) coordinate(s) in the first coordinate system corresponding to the at least one set of OCT scan parameter values.

4. The method according to claim 3, wherein:
   the received OCT retinal image data comprises OCT retinal image data of an A-scan of the retina performed by the OCT scanner; and
   the values of coordinates in the second coordinate system of pixels in the received OCT retinal image data of the A-scan are determined by:
      using said transformation and said mapping to determine the values of coordinates in the second coordinate system of a first pixel in the received OCT retinal image data of the A-scan, the first pixel being associated with a first set of OCT scan parameter values; and
      using said transformation and a vector in the first coordinate system that is indicative of a direction of a light beam incident on or propagating in the retina of the eye when the OCT scanner operates in accordance with the first set of OCT scan parameter values to determine values of coordinates in the second coordinate system of remaining pixels in the received OCT retinal image data of the A-scan.

5. The method according to claim 1, wherein determining values of coordinates in the second coordinate system of pixels in the received OCT retinal image data comprises:
   selecting a subset of pixels in the received OCT retinal image data that are distributed substantially uniformly in the received OCT retinal image data;
   determining, for each pixel of the subset of pixels, a respective value of a coordinate in the second coordinate system using the transformation from coordinates in the first coordinate system to coordinates in the second coordinate system;
   using the determined values of coordinates of pixels of the subset of pixels in the second coordinate system to determine parameters of a parameterised mapping between coordinates in the first coordinate system and coordinates in the second coordinate system; and
   using the parameterised mapping with the determined parameters to determine values of coordinates in the second coordinate system of pixels in the received OCT retinal image data.

6. The method according to claim 5, wherein the respective coordinate in the second coordinate system for each pixel of the subset of pixels is determined using:
   a first mapping for converting the coordinate of a pixel of the received OCT image data from the first coordinate system to a first real-world coordinate system;
   a second mapping for converting the coordinate of a pixel in the first real-world coordinate system to a coordinate in a second real-world coordinate system; and a third mapping for converting the coordinate of a pixel in the pixel array to a corresponding coordinate in the second real-world coordinate system.

7. A method of rendering optical coherence tomography, OCT, retinal image data, which has been acquired by an OCT scanner scanning a retina of an eye over a range of scan locations, wherein each of the scan locations is associated with a respective coordinate in a first coordinate system, and each pixel of the rendered OCT retinal image data is associated with a respective coordinate in a second coordinate system that is different from the first coordinate system, the method comprising:
receiving the OCT retinal image data acquired by the OCT scanner; and processing a pixel array using the received OCT retinal image data to generate the rendered OCT retinal image data by:
determining, for each pixel of the pixel array, a respective coordinate in the first coordinate system using a transformation from coordinates in the second coordinate system to coordinates in the first coordinate system; and
calculating values of the pixels of the pixel array by using the determined coordinates in the first coordinate system to interpolate between values of pixels of the received OCT retinal image data.

8. The method according to claim 7, wherein the respective coordinate in the first coordinate system for each pixel of the pixel array is determined using:
a first mapping for converting the coordinate of the pixel of the pixel array in the second coordinate system to a coordinate in a first real-world coordinate system;
a second mapping for converting the coordinate of the pixel of the pixel array in the first real-world coordinate system to a coordinate in a second real-world coordinate system;
a third mapping for converting the coordinate of the pixel of the pixel array in the second real-world coordinate system to a set of OCT scan parameter values indicative of a location within the scan performed by the OCT scanner; and
a fourth mapping for converting the set of OCT scan parameter values to the coordinate of the pixel of the pixel array in the first coordinate system.

9. The method according to claim 7, wherein OCT retinal image data of a plurality of OCT retinal images acquired by the OCT scanner is rendered using a common second coordinate system.

10. A non-transitory computer-readable storage medium storing computer program instructions which, when executed by a computer, cause the computer to perform a method according to claim 1.

11. A non-transitory computer-readable storage medium storing computer program instructions which, when executed by a computer, cause the computer to perform a method according to claim 2.

12. An apparatus for rendering optical coherence tomography, OCT, retinal image data, which has been acquired by an OCT scanner scanning a retina of an eye over a range of scan locations, wherein each of the scan locations is associated with a respective coordinate in a first coordinate system, and each pixel of the rendered OCT retinal image data is associated with a respective coordinate in a second coordinate system that is different from the first coordinate system, the apparatus comprising:
a communication module arranged to receive the OCT retinal image data acquired by the OCT scanner;
a coordinate-determining module arranged to determine values of coordinates in the second coordinate system of pixels in the received OCT retinal image using a transformation from coordinates in the first coordinate system to coordinates in the second coordinate system; and
an interpolation module arranged to interpolate between values of the pixels at the determined values of coordinates in the second coordinate system to calculate values of the pixels of the rendered OCT retinal image data.

13. An apparatus for rendering optical coherence tomography, OCT, retinal image data, which has been acquired by an OCT scanner scanning a retina of an eye over a range of scan locations, wherein each of the scan locations is associated with a respective coordinate in a first coordinate system, and each pixel of the rendered OCT retinal image data is associated with a respective coordinate in a second coordinate system that is different from the first coordinate system, the apparatus comprising:
a communication module arranged to receive the OCT retinal image data acquired by the OCT scanner;
a coordinate-determining module arranged to determine values of coordinates in the second coordinate system of pixels in the received OCT retinal image using a transformation from coordinates in the first coordinate system to coordinates in the second coordinate system; and
an interpolation module arranged to process a pixel array using the received OCT retinal image data to generate the rendered OCT retinal image data by:
interpolating between the determined values of coordinates in the second coordinate system to calculate values of coordinates of the pixels in the pixel array in the first coordinate system; and
using the calculated values of coordinates of the pixels in the pixel array in the first coordinate system to interpolate between values of the pixels of the received OCT retinal image data to calculate values of the pixels of the array of pixels.

14. The apparatus according to claim 12, wherein the coordinate-determining module is arranged to determine the values of coordinates in the second coordinate system of pixels in the received OCT retinal image using said transformation and a mapping between (i) at least one set of OCT scan parameter values used during the acquisition of the OCT retinal image data, each set of OCT scan parameter values being indicative of a respective location within the scan, and (ii) coordinate(s) in the first coordinate system corresponding to the at least one set of OCT scan parameter values.

15. The apparatus according to claim 14, wherein:
the communication module is arranged to receive OCT retinal image data of an A-scan of the retina performed by the OCT scanner; and
the coordinate-determining module is arranged to determine the values of coordinates in the second coordinate system of pixels in the received OCT retinal image data of the A-scan by:
using said transformation and said mapping to determine the values of coordinates in the second coordinate system of a first pixel in the received OCT retinal image data of the A-scan, the first pixel being associated with a first set of OCT scan parameter values; and
using said transformation and a vector in the first coordinate system that is indicative of a direction of a light beam incident on or propagating in the retina of the eye when the OCT scanner operates in accordance with the first set of OCT scan parameter values to determine values of coordinates in the second coordinate system of remaining pixels in the received OCT retinal image data of the A-scan.

16. The apparatus according to claim 12, wherein the coordinate-determining module is arranged to determine values of coordinates in the second coordinate system of pixels in the received OCT retinal image data by:
selecting a subset of pixels in the received OCT retinal image data that are distributed substantially uniformly in the received OCT retinal image data;
determining, for each pixel of the subset of pixels, a respective value of a coordinate in the second coordinate system using the transformation from coordinates in the first coordinate system to coordinates in the second coordinate system;
using the determined values of coordinates of pixels of the subset of pixels in the second coordinate system to determine parameters of a parameterised mapping between coordinates in the first coordinate system and coordinates in the second coordinate system; and
using the parameterised mapping with the determined parameters to determine values of coordinates in the second coordinate system of pixels in the received OCT retinal image data.

17. The apparatus according to claim 16, wherein the coordinate-determining module is arranged to determine the respective value of a coordinate in the second coordinate system for each pixel of the subset of pixels using:
a first mapping for converting the coordinate of a pixel of the received OCT image data from the first coordinate system to a first real-world coordinate system;
a second mapping for converting the coordinate of a pixel in the first real-world coordinate system to a coordinate in a second real-world coordinate system; and
a third mapping for converting the coordinate of a pixel in the pixel array to a corresponding coordinate in the second real-world coordinate system.

18. An apparatus for rendering optical coherence tomography, OCT, retinal image data, which has been acquired by an OCT scanner scanning a retina of an eye over a range of scan locations, wherein each of the scan locations is associated with a respective coordinate in a first coordinate system, and each pixel of the rendered OCT retinal image data is associated with a respective coordinate in a second coordinate system that is different from the first coordinate system, the apparatus comprising:
a communication module arranged to receive the OCT retinal image data acquired by the OCT scanner;
a coordinate-determining module arranged to determine, for each pixel of a pixel array that is to be processed to generate the rendered OCT retinal image data, a respective value of a coordinate in the first coordinate system using a transformation from coordinates in the second coordinate system to coordinates in the first coordinate system; and
an interpolation module arranged to calculate values of the pixels of the pixel array by using the determined values of coordinates in the first coordinate system to interpolate between values of pixels of the pixel array.

19. The apparatus according to claim 18, wherein the coordinate-determining module is arranged to determine the respective value of the coordinate in the first coordinate system for each pixel of the pixel array using:
a first mapping for converting the coordinate of the pixel of the pixel array in the second coordinate system to a coordinate in a first real-world coordinate system;
a second mapping for converting the coordinate of the pixel of the pixel array in the first real-world coordinate system to a coordinate in a second real-world coordinate system;
a third mapping for converting the coordinate of the pixel of the pixel array in the second real-world coordinate system to a set of OCT scan parameter values indicative of a location within the scan performed by the OCT scanner; and
a fourth mapping for converting the set of OCT scan parameter values to the coordinate of the pixel of the pixel array in the first coordinate system.

20. The apparatus according to claim 12, wherein the apparatus is arranged to render OCT retinal image data of a plurality of OCT retinal images acquired by the OCT scanner using a common second coordinate system.

* * * * *